United States Patent [19]
Mori et al.

[11] Patent Number: 5,929,109
[45] Date of Patent: Jul. 27, 1999

[54] ENHANCING AND STABILIZING AGENT OF THE ACTIVITY OF BIFIDUS FACTOR

[75] Inventors: Hiroharu Mori, Tokyo, Japan; Kakuhei Isawa, Sofia, Bulgaria; Tsutomu Kaneko, Tokyo, Japan

[73] Assignee: Meiji Milk Products Company Limited, Tokyo, Japan

[21] Appl. No.: 08/943,181

[22] Filed: Oct. 3, 1997

[30] Foreign Application Priority Data

Oct. 4, 1996 [JP] Japan .................................. 8-281628

[51] Int. Cl.$^6$ .......................... A61K 39/02; A61K 45/00; A61K 45/05
[52] U.S. Cl. ................... 514/474; 424/234.1; 424/282.1; 424/93.4; 424/246.1; 424/257.1; 435/170; 435/252.1; 435/261; 435/317.1; 426/61; 426/71; 426/72; 426/262; 426/268; 426/580; 426/590; 426/599; 426/654; 426/658; 426/800; 426/801; 514/682
[58] Field of Search .............................. 424/234.1, 282.1, 424/93.4, 246.1, 257.1; 435/110, 252.1, 261, 317.1; 426/61, 71, 72, 262, 268, 580, 590, 599, 654, 658, 800, 801; 514/682

[56] References Cited

U.S. PATENT DOCUMENTS

| | | | |
|---|---|---|---|
| 2,872,382 | 2/1959 | Keck et al. | 195/100 |
| 4,963,384 | 10/1990 | Heine et al. | 426/580 |
| 5,776,739 | 7/1998 | Aisaka et al. | 435/100 |

OTHER PUBLICATIONS

Derwent Abstracts 90–366300, "Anti–Ageing Food—Contg. Immuno–Activation Substances, Antioxidant, Bifidus factor and Natural Essential Mineral" Oct. 1990.

Gyorgy, Paul et al., "Microbiological studies on growth factor for 1. Bifidus var. pennsylvanicus.", Dept. Pedia., Univ. Penn., pp. 219–223 (1955).

Bezkoravainy, Anatoly et al., "Isolation of a glycopolypeptides fraction with *Lactobacillus bifidus* subspecies pennsylvanicus growth–promoting activity fro whole human milk casein.", Amer. Jour. Clin. Nutr., vol. 32, pp. 1428–1432 (1979).

Azuma, Norihiro et al., "Bifidus growth–promoting activity of a glycomacropeptide derived from human kappa–casein", Agric. Biol. Chem., vol. 48, No. 8, pp. 2159–2162 (1984).

Usami, Shoji et al., "Effects of pantethine of the growth of Bifidobacterium.", Nippon Nogeikagaku Kaisha, vol. 55, No. 6, pp. 499–501 (1981).

Tamura, Zenzo et al., "A probable structure of the Bifidus factor in carrot root.", Chem. Pharm. Bull., vol. 14, No. 10, p. 1191 (1966).

Saito, Tadao, "About promoting factor for growth of bifidobacterium and utility thereof.", Ann. Bull. Tohoku Welf. Univ., vol. 10, (1986).

*Primary Examiner*—Frederick Krass
*Attorney, Agent, or Firm*—Browdy and Neimark

[57] ABSTRACT

The present invention relates to an agent for enhancing and stabilizing the activity of Bifidus factor, containing at least one member selected from the group consisting of ascorbic acid, hyposulfurous acid and acetic anhydride as the effective ingredient, and by preparing the agent singly or in combination with Bifidus factor as a food and drink type or as a composition of pharmaceutical type, intestinal microflora can be ameliorated. The agent can be used as a selective medium for assaying the number of bifidobacteria.

8 Claims, 1 Drawing Sheet

ENHANCING AND STABILIZING AGENT OF THE ACTIVITY OF BIFIDUS FACTOR

FIELD OF THE INVENTION

The present invention relates to a technique for enhancing and/or stabilizing the activity of Bifidus factor; more specifically, the present invention relates to an action of ascorbic acid and the fatty acid ester thereof or the salt thereof, hyposulfurous acid or the salt thereof, and acetic anhydride on enhancing and stabilizing the activity of Bifidus factor. The present invention is utilized for ameliorating intestinal microflora by adding the substances singly or in combination with Bifidus factor to a variety of foodstuffs or is utilized for a selective medium for specifically counting the number of bifidobacteria.

BACKGROUND OF THE INVENTION

Conventional research reports concerning the intestinal microflora in breast feeding infants and infants fed with artificial milk have indicated that bifidobacteria are useful for human health. It is now confirmed that the number of bifidobacteria is significantly decreased due to gastrointestinal disorders and aging; and that the promotion of the growth of intestinal bifidobacteria is effective for the inhibition of carcinogenesis, the suppression of intestinal putrefaction, prevention of infectious diseases and the like. Therefore, the selective growth of intestinal bifidobacteria is extremely meaningful from the respect of the management of health and the prevention and treatment of various adult diseases.

From such respect, the number of foodstuffs with added of bifidobacteria (fermented milk, yogurt, etc.) has been increased recently, and from the aspect of the production of these foodstuffs and the quality control thereof, the development of a selective medium specifically counting the number of bifidobacteria in these foodstuffs is of significance.

Regarding the substance promoting the growth of bifidobacteria, namely so-called Bifidus factor, a number of substances have been investigated and reported conventionally, including for example N-acetyl glucosamine contained in mother's milk [Proc. Soc. Exp. Biol. Med., 90, 219(1955)], peptide-related substances [Am. J. Clin. Nutr., 32, 1428 (1974), Agric. Biol. Chem., 48, 2159(1984)], Carrot extracts [Japanese Journal of Agricultural Chemistry, 55, 499(1981)], Chem. Phar. Bull., (Tokyo), 14, 1191 (1966)], Sugar-related substances [Annual Bulletin of Tohoku Welfare University, 10, 313 (1986)] and the like.

SUMMARY OF THE INVENTION

However, the preparation of these substances for promoting the growth of bifidobacteria involves laborious works, and the aforementioned research works are not sufficiently satisfactory concerning the action for selectively proliferating the bifidobacteria alone. An object of the present invention is to provide a composition for promoting the growth of bifidobacteria which composition works to selectively proliferate bifidobacteria alone rapidly, and an assay system for counting the number of bifidobacteria and the like, using the composition described above.

DETAILED DESCRIPTION OF THE INVENTION

Figure 1:
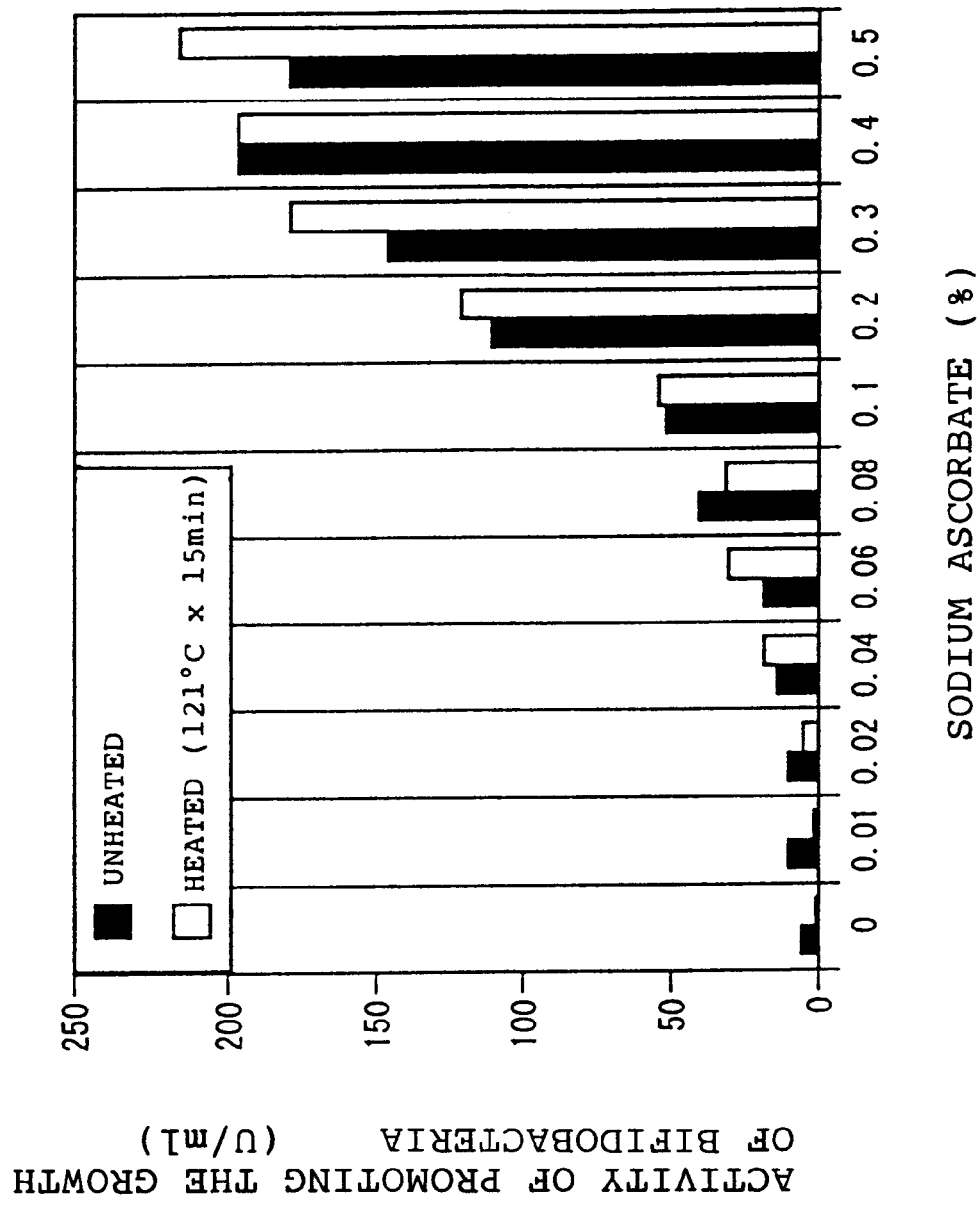
FIG. 1 depicts the activity of a filtrate of the culture of *Propionibacterium freudenreichii* ATCC 6207 strain with addition of sodium ascorbate of from 0.01 to 0.5 w/v % prior to and after heating at 121° C. for 15 minutes on promoting the growth of bifidobacteria.

In accordance with the present invention, the above object has been attained. The present inventors have made investigations on the stabilization of a microbial metabolite (Bifidus factor) which promotes the growth of bifidobacteria. Consequently, the inventors have found that ascorbic acid as one of the vitamins, and the fatty acid ester thereof or the salt thereof, hyposulfurous acid or the salt thereof, and acetic anhydride can enhance the activity of Bifidus factor and improve the thermal resistance thereof.

The present invention will now be described in detail hereinbelow. The present inventors have made screenings of a stabilizer for improving the thermal resistance of a Bifidus factor generated by bacteria of genus Propionibacterium. Then, the inventors have found that ascorbic acid, and the fatty acid ester thereof or the salt thereof, hyposulfurous acid or the salt thereof, and acetic anhydride can enhance the activity of the Bifidus factor and additionally that these substances can enhance significantly the growth promoting activity. Thus, the invention has been achieved. The inventors have found additionally that the substances can enhance the activity of Bifidus factors generated by bacteria of Bacteroidaceae, Enterobacteriaceae, Enterococcus, Lactococcus, Pediococcus and Bacillaceae other than the bacteria of the genus Propionibacterium. Based on these novel findings collected, the present inventors have made further investigations. Thus, the present invention has been achieved.

The agent to be used in accordance with the present invention (the inventive agent) includes at least one member selected from the group consisting of ascorbic acid, hyposulfurous acid (hydrosulfite) and acetic anhydride; in addition to these free acids, fatty acid esters and other various esters, alkali (earth) metal salts (sodium, potassium, calcium, magnesium salts and others) and other salts may also be used freely.

As apparent from those described below, such inventive agent significantly enhances the activity of Bifidus factor generated by not only bacteria of genus Propionibacterium but also many enteric bacteria, and therefore, the compositions containing the inventive agent are utilized as compositions for promoting the growth of bifidobacteria in the form of one member selected from pharmaceutical type, food and drink type, and assaying reagent type. By directly administering the compositions as pharmaceutical agents or directly administering or ingesting the compositions as nutrient foods or functional foods as foods for specific hygiene or by ingesting these compositions into various foods (fermented milk, yogurt or others), for example, intestinal microflora can be improved. Additionally, the compositions of the present invention can be utilized in assay systems for counting the number of bifidobacteria and the like.

In accordance with the present invention, the term "Bifidus factor" encompasses all such factors including substances isolated as chemical substances and substances from microorganisms. Examples of the former include α-naphthoquinone-related substances such as α-naphthoquinone and the derivatives thereof.

The latter Bifidus factor includes compounds generated by bacteria of Propionibacterium, Bacteroidaceae, Enterobacteriaceae, Enterococcus, Lactococcus, Pediococcus and Bacillaceae, and the compounds include pure compounds isolated and purified, crude products thereof, and those contain ing the compounds. Furthermore, the Bifidus factor includes the bacteria, culture broth (culture supernatant), and culture, which are collected from the culture of these bacteria, and the processed matters thereof (concentrates, pasty products, dried products, diluted products, etc.).

When the composition of the present invention is to be used as a pharmaceutical composition, the inventive agent should be administered in a variety of formulations. The dosage formulations include for example oral dosage forms such as tablets, capsules, granules, powders, syrups and the like; specifically, enteric coated capsules are particularly effective. According to routine methods, these formulations of various types can be prepared by using known auxiliary agents routinely used in the field of producing pharmaceutical agents, such as excipients, binders, degrading agents, lubricating agents, flavoring agents, solubilizers, suspending agents, coating agents and the like, together with the principal agent.

The formulations are preferably administered orally to humans. The therapeutically effective dose of the effective ingredient varies depending on the age and conditions of each patient, but generally, the effective ingredient should be administered orally at 1.0 to 100 mg/kg·human body weight per day. Among the substances relating to the inventive agent, ascorbic acid has no safety problem; acetic anhydride causes no toxicity concern; even on day 10 or thereafter, no death was observed in mice administered with hyposulfurous acid at 100 mg/day. Hence, it is confirmed that the substances relating to the inventive agent are all safe.

Because the inventive agent can attain the primary object if administered orally, the composition of the present invention can be used in the form of food and drink type. For such use, the inventive agent is prepared as drinks, tablets, other various foods and drinks, by using various auxiliary agents and other foods and drinks; or the inventive agent is directly added to foods and drinks. As has been described above, various methods may be utilized therefor. Because the inventive composition prepared as food and drink type can be incorporated for a prolonged term, the composition is prepared as commercially available products such as foods for specific health, nutrient agents, health foods and the like, in addition to common food and drink products.

The concurrent use of the inventive agent and the Bifidus factor exerts very high potency of promoting the growth of bifidobacteria and additionally exerts very high selectivity and specificity. In accordance with the present invention, additionally, even bifidobacteria in which growth suppressed through the presence of antibiotics and the like can recover growth potency by adding the inventive agent. Thus, the inventive agent singly or in combination with Bifidus factor is directly administered to humans or animals to increase the number of bifidobacteria in the gastrointestinal tract. In addition to the aforementioned utilization method, the inventive agent can be added together with the Bifidus factor to a selective medium for the enumeration of bifidobacterial counts in foods, colon contents and feces samples.

More specifically, as one of the systems for counting the number of bifidobacteria in a sample containing bifidobacteria, conventionally, a method has been known, comprising inoculating and incubating the sample in an agar medium containing a selective agent suppressing the growth of contaminated bacteria except bifidobacteria, thereby specifically or selectively growing bifidobacteria alone, to determine the presence or absence of bifidobacteria or viable counts of bifidobacteria. However, the selective medium with addition of the selective agent particularly at a high concentration suppresses the growth of contaminated bacteria excluding bifidobacteria but may also suppress the growth of bifidobacteria of themselves. Hence, it has been difficult to accurately determine the number of bifidobacteria.

In contrast hereto, a selective medium with addition of the inventive agent and the Bifidus factor can specifically promote the growth of bifidobacteria to induce the formation of colonies, whereby the number of bifidobacteria can be counted accurately. The effect can be exerted even if any known selective agent such as propionate salts and lithium chloride is used, other than antibiotics such as paromomycin sulfate and neomycin sulfate. Therefore, the selective medium for assaying bifidobacteria, which is produced by adding the inventive agent and the Bifidus factor to a routine medium, can be used effectively in a wide variety of assay fields.

An assay kit comprising the inventive agent and medium components and other reagents, if necessary, may be prepared and commercially available for the aforementioned use.

EXAMPLES

The present invention will now be described in the following examples.

Example 1

Action of Enhancing the Activity of Bifidus factor Generated by a Variety of Bacteria Bifidus factor-generating bacteria including propionibacteria were cultured in a TPYG medium [tripticase (BBL; 8 g), phyton peptone (BBL; 3 g), yeast extract (5 g), L-cysteine hydrochloride salt (0.5 g), glucose (20 g), $K_2HPO_4$ (2 g), $MgCl_2.6H_2O$ (0.5 g), $FeSO_4.7H_2O$ (10 mg), distilled water (1000 ml), pH 6.5] at 30° C. or 37° C. for 24 hours or 72 hours.
(a) *Propionibacterium freudenreichii* ATCC 6207 (30° C., 72 hours)
(b) *Escherichia coli* ATCC 9637 (37° C., 24 hours)
(c) *Enterobacter cloacae* ATCC 13047 (37° C., 24 hours)
(d) *Serratia liquefaciens* ATCC 27592 (37° C., 24 hours)
(e) *Bacteroides vulgatus* ATCC 8482 (37° C., 24 hours)
(f) *Enterococcus faecalis* ATCC 19433 (37° C., 24 hours)
(g) *Lactococcus lactis* subsp. *lactis* ATCC 19435 (30° C., 24 hours)
(h) *Pediococcus halophilus* ATCC 33315 (30° C., 24 hours)
(i) *Bacillus subtilis* ATCC 6051 (30° C., 24 hours)

Each of these culture broths was centrifuged to separate the culture supernatant, which was then filtered through a filter of a matrix size of 0.45 µm to recover the filtrate. To the resulting filtrate was added sodium ascorbate, sodium hyposulfite or acetic anhydride at 0.1 w/v %, and thereafter, the resulting mixture was used to assay the activity of promoting the growth of bifidobacteria. Then, the mixture was heated at 121° C. for 15 minutes. The activity was again assayed. As a control, a filtrate of a culture with no addition of the inventive agent was used. The activity of promoting the growth of bifidobacteria was assayed by the following method. More specifically, a medium for assaying the activity [tripticase (BBL; 4 g), phyton peptone (BBL; 1.5 g), yeast extract (2.5 g), L-cysteine hydrochloride salt (0.25 g), glucose (20 g), $K_2HPO_4$ (2 g), $KH_2PO_4$ (3 g), $MgCl_2.6H_2O$ (0.25 g), $FeSO_4.7H_2O$ (5 mg), agar (15 g), distilled water (1000 ml), pH 8.5] was dissolved under heating, and in the resulting medium was inoculated *Bifidobacterium longum* ATCC 15707 at 50° C. to a final concentration of $10^5$ CFU/ml. Then, 10 ml of the culture was poured into a sterilized petri dish (of a diameter of 8.5 cm), to prepare an agar plate. On the plate was placed a paper disk (of a diameter of 6 mm, thickness of 0.7 mm), having been impregnated with a sample solution and dried preliminarily, for 15-hr anaerobic culture at 37° C. (gas pack method, BBL). The diameter of a growth zone around a disk was then measured to calculate the activity of each sample on the basis of the standard curve prepared using 1-hydroxy-2-naphthoeic acid as a standard substance. The activity of 1 μg of the standard substance was defined as 1 unit.

The results are shown in Table 1 below.

TABLE 1

| | Activity of culture supernatant on promoting the growth of bifidobacteria (U/ml) | | | |
|---|---|---|---|---|
| Test bacteria | Control | Sodium ascorbate; 0.1% added | Sodium hyposulfite; 0.1% added | Acetic anhydride; 0.1% added |
| (a) | 6.44 (0.16)tt | 221.80 (232.38) | 61.50 (47.72) | 90.90 (48.88) |
| (b) | 0.06 (0.01) | 0.60 (0.25) | 0.59 (0.21) | 0.31 (0.18) |
| (c) | 0.04 (0.01) | 14.96 (3.17) | 0.52 (0.29) | 0.61 (0.37) |
| (d) | 0.06 (0.02) | 16.65 (8.25) | 2.00 (0.62) | 0.74 (0.34) |
| (e) | 0.40 (0.09) | 56.31 (21.43) | 0.68 (0.32) | 0.76 (0.56) |
| (f) | 0.03 (0.01) | 0.04 (0.14) | 0.05 (0.01) | 0.04 (0.01) |
| (g) | 0.12 (0.02) | 0.33 (1.40) | 0.13 (0.02) | 0.12 (0.02) |
| (h) | 0.01 (0.00) | 0.25 (0.10) | 0.01 (0.00) | 0.01 (0.00) |
| (i) | 0.04 (0.02) | 0.91 (0.29) | 0.13 (0.05) | 0.14 (0.08) |

*Values in parentheses show the activity on promoting the growth of bifidobacteria after heating at 121° C. for 15 minutes.

As shown in Table 1, the addition of sodium ascorbate significantly elevated the activity of the culture filtrates of various tested bacteria on promoting the growth of bifidobacteria, except *Escherichia coli* ATCC 9637 and *Enterococcus faecalis* ATCC 19433. The activity of the culture filtrates of *Enterobacter cloacae* ATCC 961, *Serratia liquefaciens* ATCC 27592, and *Bacteroides vulgatus* ATCC 8482 on promoting the growth of bifidobacteria was increased by 100-fold or more. The activity of the culture filtrates of *Escherichia coli* ATCC 9637 and *Enterococcus faecalis* ATCC 19433 on promoting the growth of bifidobacteria was significantly increased when the filtrates were heated after sodium ascorbate was added to the filtrates. Alternatively, the addition of sodium hyposulfite or acetic anhydride significantly increased the activity of the culture filtrates of various tested bacteria, except *Enterococcus faecalis* ATCC 19433, *Lactococcus lactis* ATCC 19435 and *Pediococcus halophilus* ATCC 33315, on promoting the growth of bifidobacteria.

Example 2

Concentration of Sodium Ascorbate in Addition and the Activity of the Culture Filtrate of Propionibacteria on Promoting the Growth of Bifidobacteria

*Propionibacterium freudenreichii* ATCC 6207 strain was cultured in a TPYG culture medium at 30° C. for 3 days. Sodium ascorbate was added to the resulting culture filtrate to a final concentration of 0.01 to 0.5 w/v %, which was then heated at 121° C. for 15 minutes. The activity of the culture filtrate on promoting the growth of bifidobacteria prior to and after heating was assayed by the same method as in Example 1.

As shown in FIG. 1, the activity of promoting the growth of bifidobacteria was increased greatly as the concentration of ascorbate was elevated; if the ascorbate was added at emrentrations above 0.04%, the activity did not decrease even after the culture filtrate was heated at 121° C. for 15 minutes.

Example 3

Influence of Ascorbate on the Activity of Murine Caecum Contents on Promoting the Growth of Bifidobacteria CMF feed (manufactured by oriental Yeast Co., Ltd.), 10% skimmed milk-added CMF feed, and 10% propionibacteria fermented powder (produced by culturing *Propionibacterium freudenreichii* ATCC 6207 strain in a 10% skimmed milk medium at 30° C. for 3 days and freeze-drying the resulting fermented solution)—added CMF feed were independently fed to groups of male ICR mice of age 4 weeks, each group consisting of two mice. Three weeks later, the mice of each group were autopsied to resect their caecums, followed by addition of distilled water of a 4-fold volume to prepare homogeneous solutions. The activity of these solutions on promoting the growth of bifidobacteria was assayed prior to and after sodium ascorbate was added to these solutions, to calculate the average activity per 1 g of caecum.

The results are shown in Table 2 below.

TABLE 2

| | Activity of caecum contents on promoting the growth of bifido-bacteria (U/g) | |
|---|---|---|
| Feed for administration | control | sodium ascorbate; 0.1% added |
| CMF | 0.47 | 1.19 |
| 10% skimmed milk-added CMF | 0.38 | 0.92 |
| 10% propionibacteria fermented powder-added CMF | 0.66 | 2.03 |

As shown in Table 2, the addition of 0.1% sodium ascorbate increased the activity of the caecum contents on promoting the growth of bifidobacteria by 2- to 3-fold in each of the groups. In the group fed with the propionibacteria fermented powder, compared with the remaining two groups, the activity of the caecum contents on promoting the growth of bifidobacteria was increased by about 1.5- to 2-fold.

Example 4

Granulated sugar (50 g), equal amounts of corn starch and lactose in a mixture (100 g), propionibacteria fermented powder (50 g), and L-ascorbic acid (100 g) were sufficiently mixed together. The mixture was equally divided into 100 portions, which were then packed individually in a bag to prepare 100 bags, of 3 grams each, as a healthy Bifidus factor nutrient food in a stick form. As the propionibacteria fermented powder, use was made of a spray-dry product of a fermented solution of *Propionibacterium freudenreichii* ATCC 6207 strain, which was preliminarily neutralized and cultured in a 10 w/v % skim milk medium, pH 6.0 at 30° C. for 72 hours, followed by sterilization.

EFFECTS OF THE INVENTION

Because the agent for enhancing the activity of Bifidus factor in accordance with the present invention significantly enhances the activity of Bifidus factor produced by a great number of enteric bacteria primarily including propionibacteria, the agent can be prepared singly or in combination with Bifidus factor as foods and drinks or oral formulations, which are directly administered or given to humans or animals, to effectively increase the number of bifidobacteria in the gastrointestinal tract (except acetic anhydride).

Furthermore, the agent for enhancing the activity of Bifidus factor in accordance with the present invention exerts an excellent effect of promoting the growth of bifidobacteria, singly or in combination with Bifidus factor, and additionally, the agent is so highly selective and specific that the addition of the agent together with Bifidus factor into a selective medium of bifidobacteria promotes the formation of colonies of bifidobacteria alone. The agent does not exert such effect on other contaminated bacteria. Therefore, the agent can be efficiently utilized in counting the number of viable bifidobacteria and for other various assays.

What is claimed is:

1. A method for thermally stabilizing the bifidobacterial growth promoting activity of Bifidus factor, comprising adding to Bifidus factor an effective amount of at least one stabilizing agent selected from the group consisting of ascorbic acid, salts of ascorbic acid, esters of ascorbic acid, hyposulfurous acid, salts of hyposulfurous acid, esters of hyposulfurous acid, acetic anhydride and combinations thereof;

wherein said Bifidus factor is obtained by culturing of at least one species of bacterium of a genus selected from the group consisting of Enterococcus, Propionibacteria, Bacteroidaceae, Enterobacteriaceae, Lactococcus, Pediococcus, Bacilliaceae and combinations thereof, and is selected from the group consisting of compounds; crude products comprising compounds; cells, cultures, filtrates, broths or culture supernatants of the bacterium; and processed products thereof.

2. The method of claim 1 wherein the Bifidus factor is alpha-naphthoquinone or a derivative thereof.

3. The method of claim 1 wherein the bacterium is *Propionibacterium freudenreichii*.

4. The method of claim 3 wherein the stabilizing agent is selected from the group consisting of ascorbic acid, salts thereof, and esters thereof.

5. A composition for thermally stabilizing the bifidobacterial growth promoting activity of Bifidus factor, comprising 1) Bifidus factor and 2) an effective amount of at least one stabilizing agent selected from the group consisting of ascorbic acid, salts of ascorbic acid, esters of ascorbic acid, hyposulfurous acid, salts of hyposulfurous acid, esters of hyposulfurous acid, acetic anhydride and combinations thereof;

wherein said Bifidus factor is obtained by culturing of at least one species of bacterium of a genus selected from the group consisting of Enterococcus, Propionibacteria, Bacteroidaceae, Enterobacteriaceae, Lactococcus, Pediococcus, Bacilliaceae and combinations thereof, and is selected from the group consisting of compounds; crude products comprising compounds; cells, cultures, filtrates, broths or culture supernatants of the bacterium; and processed products thereof.

6. The composition of claim 5 wherein the Bifidus factor is alpha-naphthoquinone or a derivative thereof.

7. The composition of claim 5 wherein the bacterium is *Propionibacterium freudenreichii*.

8. The composition of claim 7 wherein the stabilizing agent is selected from the group consisting of ascorbic acid, salts thereof, and esters thereof.

* * * * *